(12) United States Patent
Otaki et al.

(10) Patent No.: US 9,410,899 B2
(45) Date of Patent: Aug. 9, 2016

(54) ILLUMINATION APPARATUS AND PATTERN INSPECTION APPARATUS

(71) Applicant: NuFlare Technology, Inc., Yokohama (JP)

(72) Inventors: Toshiaki Otaki, Kanagawa (JP); Riki Ogawa, Kanagawa (JP)

(73) Assignee: NuFlare Technology, Inc., Yokohama (JP)

( * ) Notice: Subject to any disclaimer, the term of this patent is extended or adjusted under 35 U.S.C. 154(b) by 0 days.

(21) Appl. No.: 14/607,737

(22) Filed: Jan. 28, 2015

(65) Prior Publication Data
US 2015/0219568 A1  Aug. 6, 2015

(30) Foreign Application Priority Data

Feb. 3, 2014 (JP) .................. 2014-018263

(51) Int. Cl.
*G01N 21/88* (2006.01)
*G01N 21/956* (2006.01)
*G02B 26/08* (2006.01)
*G02B 5/18* (2006.01)
*G02B 27/48* (2006.01)
*G02B 26/06* (2006.01)

(52) U.S. Cl.
CPC .......... *G01N 21/8806* (2013.01); *G01N 21/956* (2013.01); *G01N 21/95607* (2013.01); *G02B 5/1871* (2013.01); *G02B 26/06* (2013.01); *G02B 26/0808* (2013.01); *G02B 27/48* (2013.01); *G01N 2021/95676* (2013.01); *G01N 2201/0638* (2013.01); *G01N 2201/06113* (2013.01)

(58) Field of Classification Search
None
See application file for complete search history.

(56) References Cited

U.S. PATENT DOCUMENTS

| 5,644,390 A * | 7/1997 | Yasuzato | G03F 7/705 355/67 |
| 7,495,779 B2 | 2/2009 | Ogawa | |
| 2004/0125459 A1* | 7/2004 | Tanitsu | G02B 3/0056 359/619 |
| 2008/0231846 A1 | 9/2008 | Ogawa | |
| 2010/0118683 A1* | 5/2010 | Choi | G11B 7/1353 369/109.01 |
| 2012/0189032 A1 | 7/2012 | Ogawa | |

FOREIGN PATENT DOCUMENTS

| JP | 2008 233342 | 10/2008 |
| JP | 2012 150036 | 8/2012 |

OTHER PUBLICATIONS

Combined Office Action and Search Report issued Jan. 13, 2016 in Taiwanese Patent Application No. 104100280 (with English language translation).
Office Action mailed Apr. 21, 2016 in Korean Application No. 10-2015-0015873 (with English Translation).

* cited by examiner

*Primary Examiner* — Gordon J Stock, Jr.
(74) *Attorney, Agent, or Firm* — Oblon, McClelland, Maier & Neustadt, L.L.P.

(57) ABSTRACT

An illumination apparatus according to embodiments includes: a light source generating laser light; a rotational phase plate having a plurality of randomly arranged stepped regions, the rotational phase plate transmitting the laser light to give a phase change to the laser light; and an integrator including a plurality of lenses arranged in an array, the laser light transmitted through the rotational phase plate being incident on the integrator, an allowable angle of incidence for the laser light of the lenses being set at a maximum value of or larger than an angle of diffraction of a first order of the laser light at the rotational phase plate.

5 Claims, 5 Drawing Sheets

ILLUMINATION APPARATUS AND PATTERN INSPECTION APPARATUS

CROSS-REFERENCE TO RELATED APPLICATION

This application is based upon and claims the benefit of priority from Japanese Patent Applications No. 2014-018263, filed on Feb. 3, 2014, the entire contents of which are incorporated herein by reference.

FIELD OF THE INVENTION

The present disclosure relates to illumination apparatuses and pattern inspection apparatuses.

BACKGROUND OF THE INVENTION

With the recent higher integration and larger capacity of large-scale integration (LSI) circuits, line widths of circuits desired for semiconductor devices have become even narrower. These semiconductor devices are manufactured, for example, in such a manner that, by using an original pattern (also referred to as a mask or a reticle; hereinafter comprehensively referred to as a mask) having a circuit pattern formed thereon, the pattern is exposed and transferred on a wafer by a reduction projection aligner referred to as a stepper, so as to form a circuit.

Improvement in yield is indispensable for the costly LSI manufacture. The yield is lowered when a defect in pattern exists in the mask to be used for transferring the pattern on semiconductor wafers. Thus, high accuracy of pattern inspection apparatuses for inspecting defects in masks for use in LSI manufacture is demanded.

In order to realize high accuracy of pattern inspection, illumination light rays with shorter wavelengths have come into use which achieve high resolution. For example, a deep ultraviolet ray of or below 200 nm in wavelength is used. Laser light, which is coherent light, is used as illumination light.

However, coherent light is highly interferential, and speckles (interference fringes) tend to occur, which adversely affects inspection accuracy. Hence, one method to reduce speckles is to pass laser light through a rotational phase plate (JP-A 2012-150036).

SUMMARY OF THE INVENTION

An illumination apparatus according to one aspect of the present disclosure includes: a light source generating laser light; a rotational phase plate having a plurality of randomly arranged stepped regions, the rotational phase plate transmitting the laser light to give a phase change to the laser light; and an integrator including a plurality of lenses arranged in an array, the laser light transmitted through the rotational phase plate being incident on the integrator, an allowable angle of incidence for the laser light of the lenses being set at a maximum value of or larger than an angle of diffraction of a first order of the laser light at the rotational phase plate.

An illumination apparatus according to one aspect of the present disclosure includes: a light source generating laser light; a rotational phase plate having a plurality of randomly arranged stepped regions, the rotational phase plate transmitting the laser light to give a phase change to the laser light; and an integrator including a plurality of lenses arranged in an array, the laser light transmitted through the rotational phase plate being incident on the integrator, wherein a relationship of Equation (1) is established where $\lambda$ is the peak wavelength of the laser light, d is the minimum pitch of the stepped regions, D is the effective diameter of the lenses, and f is the focal distance of the lenses:

$$\sin^{-1}(\lambda/d) \le \tan^{-1}(D/2f) \qquad \text{Equation (1).}$$

A pattern inspection apparatus according to the above aspect includes: a light source generating laser light; a rotational phase plate having a plurality of randomly arranged stepped regions, the rotational phase plate transmitting the laser light to give a phase change to the laser light; an integrator including a plurality of lenses arranged in an array, the laser light transmitted through the rotational phase plate being incident on the integrator, an allowable angle of incidence for the laser light of the lenses being set at a maximum value of or larger than an angle of diffraction of a first order of the laser light at the rotational phase plate; an optical image obtainer configured to illuminate a substrate with a pattern formed thereon by using the laser light transmitted by the integrator as illumination light, in such a manner as to obtain an optical image of the pattern; and a comparator configured to compare the optical image with a reference image.

DETAILED DESCRIPTION OF THE EMBODIMENTS

Embodiments of the present invention are described below with reference to the drawings.

First Embodiment

An illumination apparatus according to a first embodiment includes: a light source configured to generate laser light; a rotational phase plate having a plurality of randomly arranged stepped regions, the rotational phase plate being configured to transmit the laser light to give a phase change thereto; and an integrator including a plurality of lenses arranged in an array, the integrator being configured to allow the laser light transmitted by the rotational phase plate to be incident thereon, wherein the lenses have an allowable angle of incidence for the laser light being set at a maximum value of or larger than an angle of diffraction of the first order of the laser light at the rotational phase plate.

Figure 1:
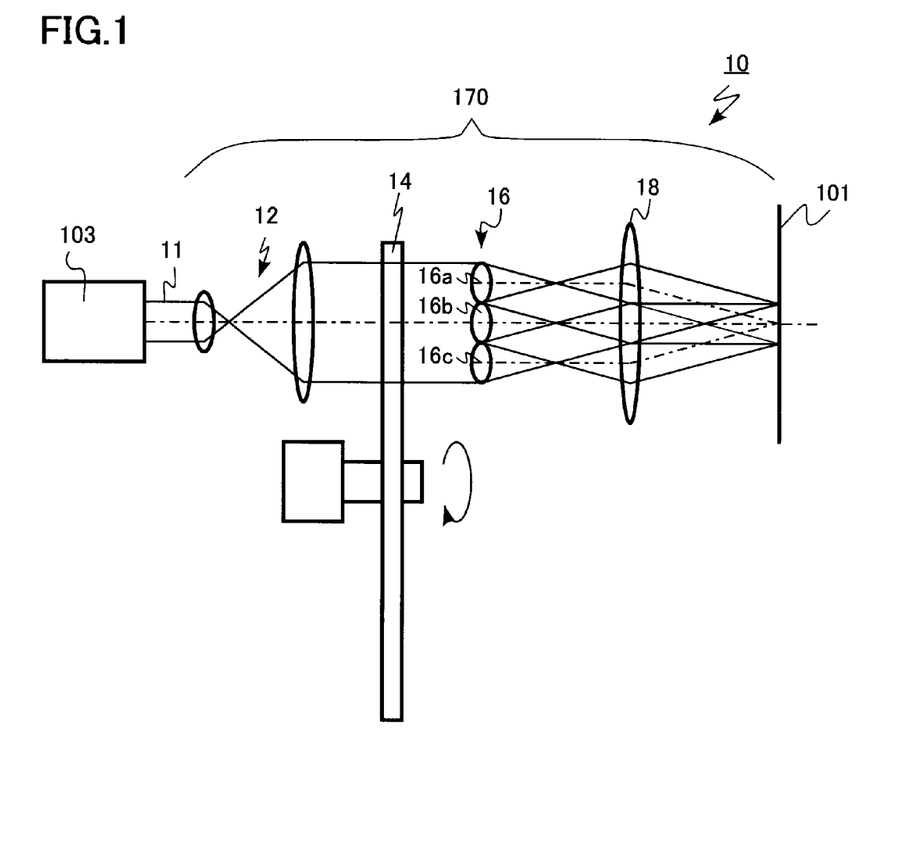
FIG. 1 is a configuration diagram of an illumination apparatus according to a first embodiment.

FIG. 1 is a configuration diagram of an illumination apparatus according to the first embodiment. The illumination apparatus according to the first embodiment is used with a pattern inspection apparatus for inspecting masks.

An illumination apparatus 10 according to the first embodiment includes a light source 103 and an illumination optical system 170. The illumination optical system 170 includes a beam expander 12, a rotational phase plate 14, an integrator 16, and a condenser lens 18.

The light source 103 serves as a light source of illumination light for pattern inspection. The light source 103 generates laser light 11, which is coherent light, as illumination light.

The light source 103 generates, for example, ArF excimer laser having a peak wavelength (λ) of 193 nm. The peak wavelength (λ) of the laser light 11 is desirably in a range from 10 nm to 200 nm from the viewpoint of enhancing accuracy of pattern inspection.

The beam expander 12 expands the laser light 11 emitted from the light source 103. The beam expander 12 comprises, for example, two lenses.

Figure 2A:
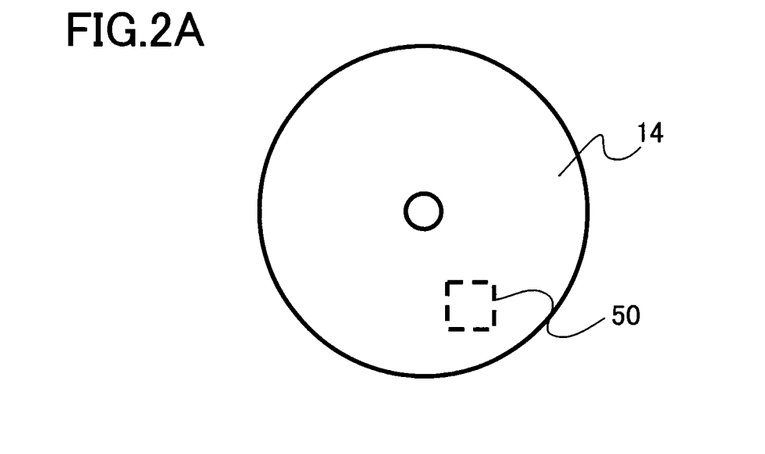
FIGS. 2A, 2B, and 2C are conceptual diagrams of a rotational phase plate of the first embodiment.
Figure 2B:
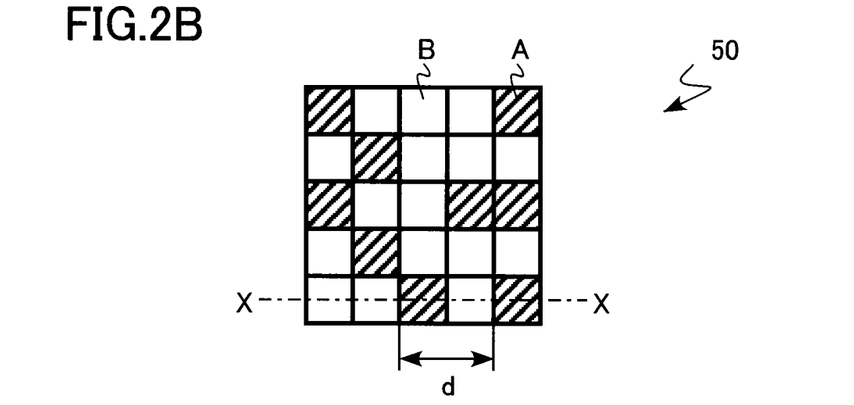
Figure 2C:
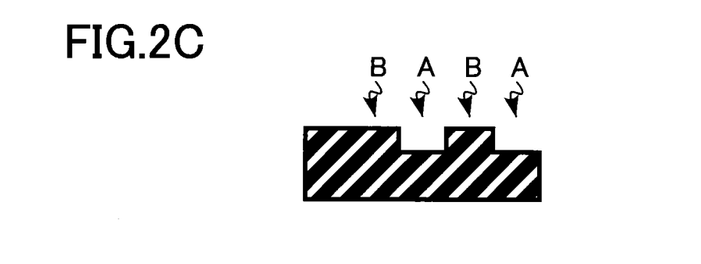

FIGS. 2A, 2B, and 2C are conceptual diagrams of the rotational phase plate of the present embodiment. FIG. 2A is a top view, FIG. 2B is an enlarged view of a region 50 enclosed with a dotted line frame in FIG. 2A, and FIG. 2C is a cross-sectional view taken along line X-X in FIG. 2B.

Enlarging the region 50 of the rotational phase plate 14 depicted in FIG. 2A reveals that, as depicted in FIG. 2B, a plurality of stepped regions A is randomly arranged on the surface. As depicted in FIG. 2C, the stepped regions A are portions carved to a depth corresponding to or smaller than the wavelength (λ) of the laser light relative to adjacent non-stepped regions B.

The rotational phase plate 14 is rotated at a high speed with respect to a rotation axis by a motor (not shown). The number of rotations of the rotational phase plate is, for example, in a range from 5000 rotations per minute (rpm) to 20000 rpm.

The laser light 11 that is incident on the rotational phase plate perpendicularly thereto has a phase changed depending on whether the light passes through the stepped regions A or through the non-stepped regions B. This allows the phase of the laser light to be applied to a mask 101 (FIG. 1) (an inspection object) to be temporally changed, and speckles are thus reduced.

It is to be noted here that, as depicted in FIG. 2B, a minimum pitch of the stepped regions A is defined as d. The minimum pitch d is desirably sufficiently small to reduce speckles. The minimum pitch d is desirably in a range from 1 μm to 100 μm.

The integrator 16 has a plurality of lenses 16a, 16b, and 16c arranged in an array. The lenses 16a, 16b, and 16c comprising the integrator 16 are not particularly limited. For example, the lenses may be rod lenses or composite lenses each comprising two lenses. The lenses 16a, 16b, and 16c comprising the integrator 16 are telecentric at the image side.

The laser light 11 transmitted by the rotational phase plate 14 is inputted to the integrator 16. Because the laser light 11 transmit the integrator 16, homogeneity in intensity of illumination of the illumination light to be applied to the mask 101 improves.

The condenser lens 18 has a function of concentrating the laser light 11. The laser light 11 transmitted by the integrator 16 is concentrated by the condenser lens 18 and applied to the mask 101.

Figure 3:
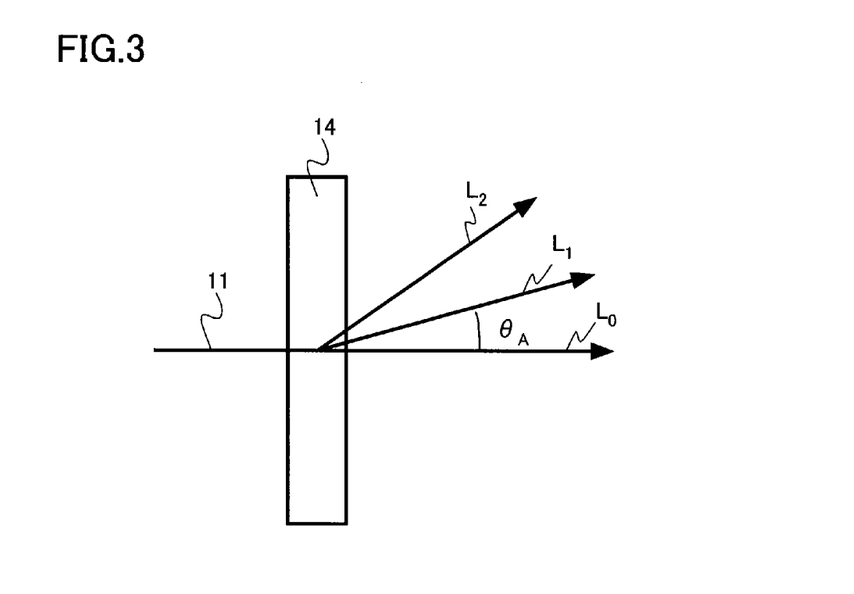
FIG. 3 is an explanatory diagram of an action of the first embodiment.
Figure 4:
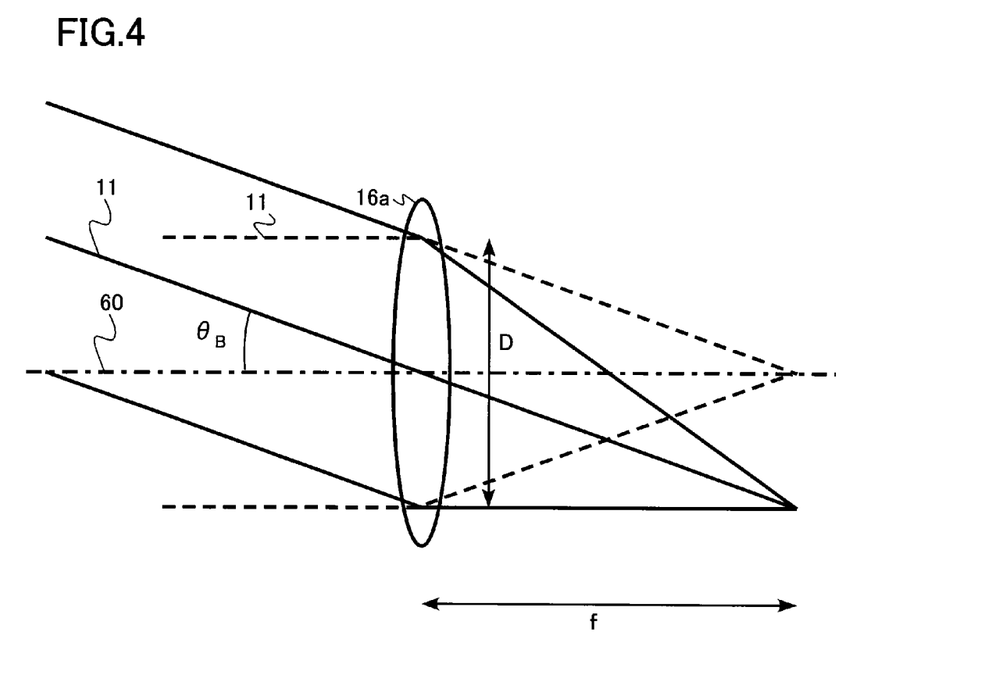
FIG. 4 is an explanatory diagram of an action of the first embodiment.

FIGS. 3 and 4 are explanatory diagrams of functions of the present embodiment. FIG. 3 is an explanatory diagram of an angle of diffraction at the rotational phase plate 14. FIG. 4 is an explanatory diagram of an allowable angle of incidence of the integrator 16.

FIG. 3 is an enlarged view of a partial region of the rotational phase plate 14. The rotational phase plate 14 has the stepped regions A so as to function as a diffraction grating as well. Thus, as depicted in FIG. 3, the laser light 11 that is incident on the surface of the rotational phase plate 14 perpendicularly thereto passes through the rotational phase plate 14, so as to be branched into rectilinear light $L_0$, primary diffracted light $L_1$, secondary diffracted light $L_2$, and further diffracted light of or higher than the third order (not shown).

It is to be noted here that the angle formed by the rectilinear light $L_0$ and the primary diffracted light $L_1$ is an angle of diffraction of the first order, and the angle of diffraction of the first order is indicated by $\theta_A$. The angle of diffraction of the first order $\theta_A$ is actually measurable by directly observing the pattern of the laser light 11 passing through the rotational phase plate 14.

Further, the angle of diffraction of the first order $\theta_A$ has a maximum value represented by $$\sin^{-1}(\lambda/d) \hspace{4cm} \text{Equation (2)}$$

where λ is the peak wavelength of the laser light and d is the minimum pitch of the stepped regions A.

FIG. 4 is an enlarged view of one lens 16a of the lenses comprising the integrator 16. The lens 16a can output only incident light that is in a certain angle range with respect to an optical axis 60. The maximum value of this angle range is defined as an allowable angle of incidence $\theta_B$ of the integrator 16.

The light that is incident on the lens 16a at an angle larger than the allowable angle of incidence $\theta_B$ becomes, for example, stray light within the lens 16a and is not outputted from the lens 16a. Hence, the incident light at an angle larger than the allowable angle of incidence $\theta_B$ of the integrator 16 makes a loss of the quantity of light without reaching a desired position on the mask 101. Thus, the quantity of light on the radiated surface is reduced by that loss. Reduction in quantity of light on the radiated surface leads to lowering of inspection accuracy for defects.

The allowable angle of incidence $\theta_B$ is a characteristic value of the lens 16a. The allowable angle of incidence $\theta_B$ is represented by $$\tan^{-1}(D/2f) \hspace{4cm} \text{Equation (3)}$$

where D is the effective diameter of the lens 16a and f is the focal distance of the lens. It is to be noted that the effective diameter of the lens is a value indicating a range of outgoing light from the focal point of the lens becoming parallel light after passing through the lens.

In the illumination apparatus 10 according to the present embodiment, the allowable angle of incidence $\theta_B$ for the laser light 11 of the integrator 16 is set at or larger than the maximum value of the angle of diffraction of the first order $\theta_A$ of the laser light 11 at the rotational phase plate 14. In other words, as derived from Equations (2) and (3), the relationship as represented by Equation (1) is established where λ is the peak wavelength of the laser light, d is the minimum pitch of the stepped regions A, D is the effective diameter of the lens, and f is the focal distance of the lens.

$$\sin^{-1}(\lambda/d) \leq \tan^{-1}(D/2f) \hspace{3cm} \text{Equation (1)}$$

Description is given of functions of the illumination apparatus 10 according to the present embodiment. According to the present embodiment, the rotational phase plate 14 is provided to reduce speckles. At the same time, the integrator 16 is provided to increase homogeneity in intensity of illumination of the illumination light.

However, as described above, since the rotational phase plate 14 also functions as a diffraction grating, diffracted light is generated. Further, the integrator 16 has the allowable angle of incidence $\theta_B$. When the angle of diffraction of the diffracted light exceeds the allowable angle of incidence $\theta_B$, a loss of quantity of light eventuates.

In the illumination apparatus 10 according to the present embodiment, as described above, the allowable angle of incidence $\theta_B$ for the laser light 11 of the integrator 16 is set at or larger than the maximum value of the angle of diffraction of the first order $\theta_A$ of the laser light 11 at the rotational phase plate 14. In other words, as derived from Equations (2) and (3), the relationship as represented by Equation (1) is established where $\lambda$ is the peak wavelength of the laser light, d is the minimum pitch of the stepped regions A, D is the effective diameter of the lenses, and f is the focal distance of the lenses.

$$\sin^{-1}(\lambda/d) \leq \tan^{-1}(D/2f) \quad \text{Equation (1)}$$

With this configuration, at least the primary diffracted light at the rotational phase plate 14 is inputted to the integrator 16 and is effectively outputted therefrom, so as to reach the surface of the mask 101. Hence, the loss of quantity of light at the integrator 16 is suppressed. Accordingly, an illumination apparatus is achieved which compatibly provides for reduction of speckles and an ensured quantity of light.

It is to be noted that the peak wavelength $\lambda$ of the laser light 11 is desirably as short a wavelength as possible in order to enhance accuracy of inspection. The peak wavelength $\lambda$ is desirably in a range from 10 nm to 200 nm.

For a shorter wavelength $\lambda$, the minimum pitch d of the stepped regions A is desirably even smaller in order to reduce speckles. In this case, as apparent from Equation (2), the maximum value of the angle of diffraction of the first order $\theta_A$ becomes larger, which emphasizes the loss of quantity of light. Hence, the configuration of the illumination apparatus satisfying Equation (1) is even more desired in order to enhance the accuracy of inspection.

Further, a smaller width at half maximum (full width at half maximum) at the peak of the laser light 11 is desired as well as the shorter wavelength of the peak wavelength $\lambda$ of the laser light 11 in order to enhance the accuracy of inspection. The width at half maximum at the peak of the laser light 11 is desirably not larger than $\lambda/10000$.

The smaller width at half maximum (full width at half maximum) increases coherence of the laser light 11. Hence, an even smaller minimum pitch d of the stepped regions A is desired in order to reduce speckles. In this case, the configuration of the illumination apparatus satisfying Equation (1) is even more desired in order to enhance the accuracy of inspection.

Second Embodiment

A pattern inspection apparatus according to a second embodiment includes: a light source configured to generate laser light; a rotational phase plate having a plurality of randomly arranged stepped regions, the rotational phase plate being configured to transmit the laser light to give a phase change thereto; an integrator including a plurality of lenses arranged in an array, the integrator being configured to allow the laser light transmitted by the rotational phase plate to be incident thereon, wherein the lenses have an allowable angle of incidence for the laser light being set at an angle of diffraction of the first order of the laser light at the rotational phase plate; an optical image obtainer configured to illuminate a substrate with a pattern formed thereon by using the laser light transmitted by the integrator as illumination light, in such a manner as to obtain an optical image of the pattern; and a comparator configured to compare the optical image with a reference image.

The pattern inspection apparatus according to the second embodiment includes the illumination apparatus according to the first embodiment. Hence, details overlapping those of the first embodiment are not described redundantly.

Figure 5:
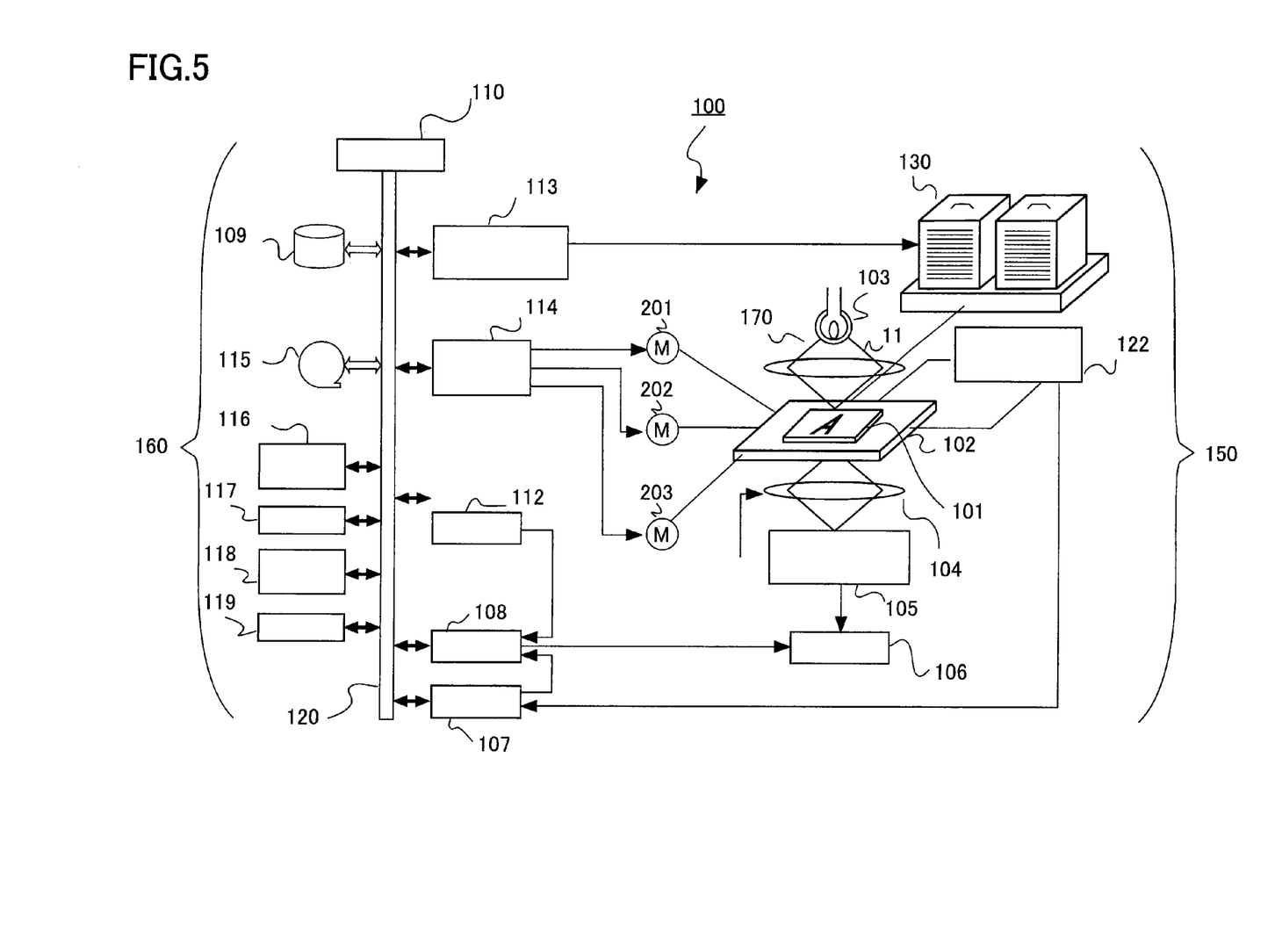
FIG. 5 is a conceptual diagram depicting the overall configuration of a pattern inspection apparatus according to a second embodiment.

FIG. 5 is a conceptual diagram depicting the overall configuration of the pattern inspection apparatus according to the second embodiment. A pattern inspection apparatus 100 according to the second embodiment is a mask inspection apparatus with which the inspection object is the mask 101. The pattern inspection apparatus 100 includes the light source 103, the illumination optical system 170, an optical image obtainer 150, and a control circuit 160.

The optical image obtainer 150 includes an XYθ table 102, a magnification optical system 104, a photodiode array 105, a sensor circuit 106, a laser measurement system 122, and an automatic loader 130. Further, in the control circuit 160, a control computer 110, which is a computer, is connected through a bus 120 serving as a data transmission path to a position circuit 107, a comparator circuit 108 exemplifying the comparator, a design image creation circuit 112, an automatic loader control circuit 113, a table control circuit 114, a magnetic disk memory device 109 exemplifying a memory device, a magnetic tape memory device 115, a flexible disk drive (FD) 116, a cathode-ray tube (CRT) 117, a pattern monitor 118, and a printer 119. The XYθ table 102 is driven by an X-axis motor 201, a Y-axis motor 202, and a θ-axis motor 203.

In the pattern inspection apparatus 100 according to the present embodiment, the light source 103 and the illumination optical system 170 have the same configuration as that of the illumination apparatus 10 described in the first embodiment.

FIG. 5 depicts constituent portions relevant to the description of the present embodiment. Needless to say, the pattern inspection apparatus 100 may include other features that are typically equipped.

Next, description is given of a method of inspecting a defect in the mask 101 by using the pattern inspection apparatus 100 according to the present embodiment.

Prior to the start of an inspection, a mask 101 with a pattern formed thereon is first loaded on the XYθ table 102 by the automatic loader 130 that is controlled by the automatic loader control circuit 113. The XYθ table 102 is disposed so as to be movable in a horizontal direction and a direction of rotation by way of motors associated with the XYθ axes. Information on a design pattern (design pattern data) used when forming the pattern on the mask 101 is inputted from the outside of the apparatus into the pattern inspection apparatus 100, so as to be stored on a magnetic disk drive 109 exemplifying the memory device (memory).

The XYθ table 102 is driven by the table control circuit 114 under the control of the control computer 110. The XYθ table 102 is movable by way of driving systems such as three-axes motors 201, 202, and 203 configured to give a drive in the X, Y, and θ directions. These X-axis motor 201, Y-axis motor 202, and θ-axis motor 203 may be, for example, stepping motors.

The position to which the XYθ table 102 is moved is measured by the laser measurement system 122 and is fed to the position circuit 107. Further, the mask 101 on the XYθ table 102 is automatically conveyed from the automatic loader 130 to be driven by the automatic loader control circuit 113 and is automatically discharged on completion of the inspection. The magnification optical system 104 is, for example, driven by a device such as a piezoelectric crystal device, and an image is focused into the photodiode array 105 by the magnification optical system 104.

Figure 6:
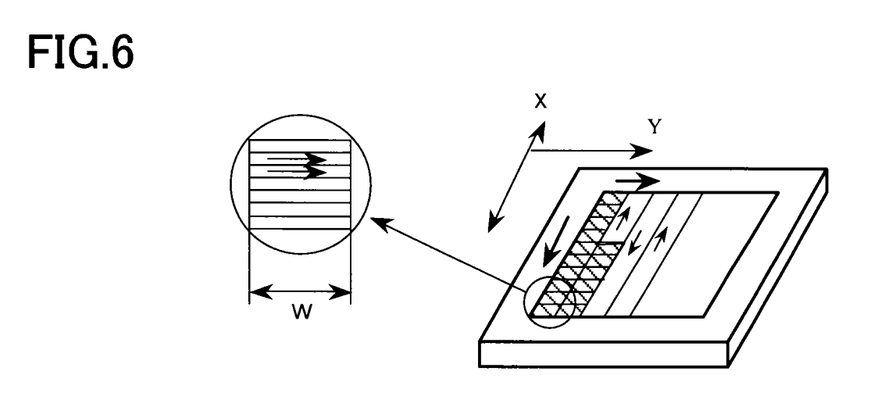
FIG. 6 is an explanatory diagram of a procedure for obtaining an optical image according to the second embodiment.

FIG. 6 is an explanatory diagram of a procedure for obtaining an optical image according to the present embodiment. A region to be inspected is, as depicted in FIG. 6, virtually divided into a plurality of inspection stripes in the form of strips with a scan width W, for example, in the Y direction. The operation of the XYθ table 102 is controlled such that the inspection stripes further divided are scanned successively, and an optical image is obtained with the scanning performed in the X direction.

Images with the scan width W as depicted in FIG. 6 are successively inputted in the photodiode array 105. After an image in a first inspection stripe is obtained, an image in a second inspection stripe is scanned in a reverse direction in turn, so as to likewise input an image with the scan width W successively. Then, in case where an image in a third inspection stripe is to be obtained, the image is obtained with the scanning performed in a reverse direction with respect to the second inspection stripe, i.e., in the direction in which the image in the first inspection stripe has been obtained. Thus, wasteful processing time is cut by obtaining images successively.

The pattern formed on the mask 101 is irradiated with light by the light source 103 that is located above the XYθ table 102. The laser light 11 emitted from the light source 103 is applied to the mask 101 through the illumination optical system 170. The light that has passed through the mask 101 by illumination forms an optical image on the photodiode array 105 by way of the magnification optical system 104 and is incident on the photodiode array 105. The image of the pattern formed on the photodiode array 105 is photoelectrically converted by the photodiode array 105 and is further subjected to analog/digital (A/D) conversion by the sensor circuit 106. For example, a sensor such as a time delay integration (TDI) sensor is installed on the photodiode array 105. In the manner as described above, the optical image obtainer 150 obtains optical image data (stripe data) per inspection stripe of the material to be inspected.

The measurement data (optical image data) of the inspection stripes outputted to the sensor circuit 106 is sequentially outputted per inspection stripe to the comparator circuit 108 together with data that has been outputted from the position circuit 107 and indicates the position of the mask 101 on the XYθ table 102. The measurement data is data without signs of, for example, 8 bit per pixel and represents the gradation of brightness of each pixel in, for example, 0 to 255. These light source 103, illumination optical system 170, magnification optical system 104, photodiode array 105, and sensor circuit 106 configure an inspection optical system of high magnification.

A design image creation circuit (reference image creator) 112 reads out the design pattern data per predetermined region from the magnetic disk drive 109 by way of the control computer 110, and converts (expands) the read design pattern data of the photomask 101 to design image data (reference image data), which is binary or multi-value image data. The predetermined region may be the region (area) of the image corresponding to the optical image to be compared. The created reference image data is outputted to the comparator circuit 108.

The figures comprising patterns defined in the design pattern data are primarily rectangles and triangles. The design pattern data retains, for example, figure data that defines, for example, the shapes, sizes, and positions of the figures of each pattern. The figure data is defined by information including coordinates (x, y) at the reference positions of the figures, the lengths of sides, and figure codes serving as identifiers for distinguishing the types of figures such as rectangles and triangles.

When such figure data is inputted to the design image creation circuit 112, the data is expanded up to data per figure, and interpretation is performed on, for example, the figure code indicating the shape of the figure and the dimensions of the figure of the figure data. Then, binary or multi-value image data is obtained from expansion as a pattern to be arranged into squares in unit of grids of predetermined quantization dimensions. The expanded image data (expansion image data) is stored on a pattern memory (not shown) in the circuit or in the magnetic disk drive 109. In other words, the design pattern data is read, and the occupancy of the figures in the design pattern is calculated per square, where the squares are resultants of virtual division of the inspection region into squares in unit of predetermined dimensions. And then the n-bit occupancy data is outputted to the pattern memory (not shown) or to the magnetic disk drive 109. For example, one square is suitably set as one pixel. Provided that one pixel is assigned with resolution of $1/2^8$ (=1/256), in case where the resolution of 1/256 is given for the regions of the figures arranged in the pixel, small regions of 1/256 are allocated to the regions of the figures arranged in the pixel, thus allowing the occupancy in the pixel to be calculated. The expanded image data is stored on the pattern memory or in the magnetic disk drive 109 as image data in area unit that is reduced by the 8-bit occupancy data with respect to each pixel.

Then, data processing (image processing) is performed on the expanded image data, such that the data is treated with appropriate file processing. The optical image data (measurement data) is in a filtered condition due to resolution characteristics of the magnification optical system 104 or the aperture effect of the photodiode array 105, in other words, in an analog condition that is subject to continuous change. Thus, filtering processing following a predetermined model is performed also on the expansion image data, which is image data on the design side with the image intensity (gray value) in digital value, such that the expansion image data is adapted to the measurement data. For example, the filtering processing to be performed includes resizing processing of enlargement or contraction, corner rounding processing, and vignetting processing. The design image data is created in this manner.

Then, in the comparator circuit 108, the optical image data per stripe is read out, and the optical image data is cut up so as to be an image in the region of the same size as that of the reference data. The comparator circuit 108 aligns the associated optical image data and reference data under a predetermined condition for determination, so as to perform comparison on a pixel-to-pixel basis. Such an inspection technique belongs to die to database inspection. Then, results of the comparison are outputted. The results of the comparison may be outputted by the magnetic disk drive 109, the magnetic tape memory device 115, the flexible disk drive (FD) 116, the CRT 117, the pattern monitor 118, or the printer 119. It is to be noted that the pattern inspection apparatus 100 according to the present embodiment may be used to perform die to die inspection wherein comparison is performed between optical image data.

The inspection for defects in the pattern of the mask 101 is performed in the above-described manner.

The pattern inspection apparatus 100 according to the present embodiment includes the illumination apparatus 10 described in the first embodiment. Hence, illumination light is achieved which provides reduction of speckles and an ensured quantity of light at the same time. Thus, a pattern inspection apparatus with enhanced accuracy for inspecting defects is achieved. Especially, higher inspection accuracy is attained in regions with a shorter laser light wavelength and a smaller width at half maximum.

Embodiments of the present invention are described above with reference to specific examples. The foregoing embodiments are given for an illustrative purpose and not for a restrictive purpose. Further, components of the embodiments may be appropriately combined.

For example, while a mask inspection apparatus for inspecting defects in patterns on masks is taken as an example of the pattern inspection apparatus in the embodiments, the present disclosure is applicable to a wafer inspection apparatus for inspecting defects in patterns on wafers.

In the embodiments, description is not given of parts and portions which are not directly relevant to the description of the present disclosure, such as the configuration of the apparatus or the manufacturing method; however, a configuration of an apparatus or a manufacturing method may be appropriately selected for use as needed. In addition, the scope of the present disclosure encompasses any illumination apparatus and pattern inspection apparatus that include elements of the present disclosure and that are of an appropriate design choice for those skilled in the art. The scope of the present disclosure is defined by the appended claims and equivalents thereof.

What is claimed is:

1. An illumination apparatus comprising:
    a light source generating laser light;
    a rotational phase plate having a plurality of randomly arranged stepped regions, the rotational phase plate transmitting the laser light to give a phase change to the laser light; and
    an integrator including a plurality of lenses arranged in an array, the laser light transmitted through the rotational phase plate being incident on the integrator, wherein
    a relationship of Equation (1) is established where $\lambda$ is the peak wavelength of the laser light, d is a minimum pitch of the stepped regions, D is the effective diameter of the lenses, and f is the focal distance of the lenses:

$$\sin^{-1}(\lambda/d) \leq \tan^{-1}(D/2f) \qquad \text{Equation(1)}.$$

2. The illumination apparatus according to claim 1, wherein the peak wavelength of the laser light is in a range from 10 nm to 200 nm.

3. The illumination apparatus according to claim 2, wherein the laser light has a full width at half maximum at a peak of $\lambda/10000$ or smaller.

4. The illumination apparatus according to claim 1, wherein the minimum pitch is in a range from 10 μm to 100 μm.

5. The illumination apparatus according to claim 1, wherein the lenses are rod lenses.

* * * * *